United States Patent [19]

Berger et al.

[11] 4,331,760
[45] May 25, 1982

[54] DIAGNOSTIC AGENT FOR THE DETECTION OF LEUKOCYTES AND CHROMOGENS USEFUL THEREIN

[75] Inventors: Dieter Berger, Viernheim; Franz Braun, Rimbach; Günter Frey, Ludwigshafen am Rhein; Werner Güthlein, Mannheim-Neckarau; Wolfgang Werner, Mannheim-Vogelstang, all of Fed. Rep. of Germany

[73] Assignee: Boehringer Mannheim GmbH, Mannheim, Fed. Rep. of Germany

[21] Appl. No.: 42,393

[22] Filed: May 25, 1979

[30] Foreign Application Priority Data

Jun. 20, 1978 [DE] Fed. Rep. of Germany ....... 2826965

[51] Int. Cl.³ .................... C12Q 1/44; C07D 327/04; G01N 33/48; G01N 33/50
[52] U.S. Cl. .................................. 435/19; 23/230 R; 23/230 B; 252/408; 422/56; 435/20; 435/21; 549/33; 549/40; 260/112 T; 260/112.5 R
[58] Field of Search ............................ 422/56; 252/408; 23/230 B, 230 R; 435/19, 20, 21; 549/40, 33, 31, 32; 260/112 T, 112.5 R

[56] References Cited

U.S. PATENT DOCUMENTS

| | | | |
|---|---|---|---|
| 1,786,611 | 12/1930 | Harden | 549/33 |
| 3,301,870 | 1/1967 | Terzijska et al. | 549/32 |
| 3,689,364 | 9/1972 | Hartel et al. | 435/19 |
| 3,741,875 | 6/1973 | Ansley et al. | 435/19 |
| 4,045,290 | 8/1977 | Bulbenko et al. | 435/21 |
| 4,046,514 | 9/1977 | Johnston et al. | 435/20 |

FOREIGN PATENT DOCUMENTS

| | | | |
|---|---|---|---|
| 722579 | 11/1965 | Canada | 435/21 |
| 50-147987 | 11/1975 | Japan | 435/21 |
| 397921 | 2/1966 | Switzerland | 549/33 |

OTHER PUBLICATIONS

Körbl, J. et al., Chem. and Ind., pp. 1624–1625 (Dec. 14, 1957).
Orndorff, W. R., et al., J.A.C.S., vol. 45, pp. 486–500, (1923).

Primary Examiner—Teddy S. Gron
Attorney, Agent, or Firm—Sprung, Felfe, Horn, Lynch & Kramer

[57] ABSTRACT

Diagnostic agent for the detection of leukocytes in body fluids, comprising an absorbent carrier which is impregnated with a chromogen and a buffer substance, wherein the chromogen is a sulfonphthalein ester of the formula

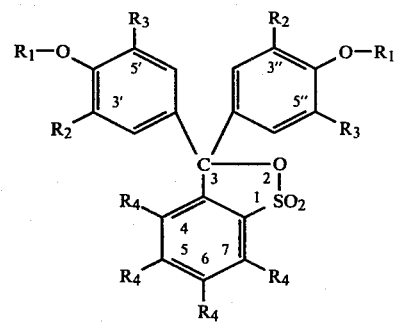

wherein
$R_1$ is a carboxylic acid residue optionally substituted by halogen or lower alkoxy; or is an amino acid or peptide residue having a nitrogen protective group;
$R_2$ is a halogen atom or a lower alkyl radical; and
$R_3$ and $R_4$ are individually selected from hydrogen and halogen.

Certain of the chromogen are provided as novel compounds.

9 Claims, No Drawings

DIAGNOSTIC AGENT FOR THE DETECTION OF LEUKOCYTES AND CHROMOGENS USEFUL THEREIN

The present invention is concerned with an agent for the detection of leukocytes in body fluids. More specifically, the invention relates to the detection of leukocytes in body fluids using chromogens and, in additional aspect, with the preparation of such chromogens.

The detection of leukocytes in body fluids and especially in urine occupies an important place in the diagnosis of diseases of the kidney and urogenital tract.

Up to the present, this detection has been carried out by the laborious counting of the leukocytes in non-centrifuged urine or in urinary sediments. It is, of course, a common feature of both methods that only intact leukocytes are counted. On the other hand, it is known that the speed of leukocyte lysis is, depending upon the urinary medium, subjected to enormous variations so that, for example, in strongly alkaline urine the leukocyte half life might be only about 60 minutes. The result is too low a leukocyte count or, in cases in which the urine has been left to stand for quite a long time, even falsely negative findings.

Apart from errors due to lysis, the quantitative microscopic determination of the leukocytes in non-centrifuged, homogenized urine gives, in a counting chamber, very dependable results. However, in practice, this method is rarely used since it is laborious, tiring and time-consuming and requires the employment of trained personnel.

The overwhelming majority of leukocyte determinations in the urine are, in medical practice, carried out by the visible field in the urine sediment. For this purpose, the material to be investigated (sediment) must be obtained by centrifuging. However, other components in the urine are thereby also enriched, for example epithelial cells and salts, which can make microscopic counting of the leukocytes considerably more difficult. Varying content of sediment, inhomogeneities of the sediment, as well as, in some cases, differing microscopic enlargement or differing optical equipment of the microscope have the result that the here usual "quantitative" statement of the number of leukocytes per microscopic visible field can include errors of several hundred percent.

Therefore, it is an object of the present invention to provide a diagnostic agent with which the leukocytes in body fluids can be detected in a simple and readily usuable manner, as well as quickly and completely.

One possible detection principle for such a leukocyte test could be an enzymatic reaction since leukocytes possess a very wide enzymatic spectrum.

U.S. Pat. No. 3,087,794 describes a leukocyte detection method which is carried out via the peroxidate activity present in the granular leukocytes (granulocytes). An absorbent carrier which is impregnated with hydrogen peroxide and an organic indicator, for example o-tolidine, indicates the presence of leukocytes by the formation of a colored oxidation product. However, such a test suffers from important disadvantages. On the one hand, peroxidate reactions quite generally possess a marked tendency to be disturbed by reducing substances present in the urine, for example ascorbic acid. On the other hand, there are many references in the literature (see, for example L. Mettler, Med. Welt, 23, 399/1972) to the instability of leukocyte peroxidase in the urine medium, which gives rise to falsely negative findings.

For some years, colorimetric methods of detection which depend upon the esterolytic activity of enzymes present in the systems to be determined have found a firm place in histochemical and cytochemical enzymology (cf. for example A. G. E. Pearse, Histochemistry, Theoretical and Applied). In principle, colorless or weakly colored esters are thereby employed which, due to enzymatic splitting, mostly break down into a colorless acid component and an also colorless alcohol or phenol component. The latter is then reacted to give colored products in a reaction following the enzymatic saponification, for example by coupling with diazonium salts or by oxidative reactions.

Thus, for example, F. Schmalzl and H. Braunsteiner (Klin. Wschr., 46, 642(1968)) describe a specific cytochemical leukocyte esterase detection with naphthol-AS-D-chloroacetate as substrate and a diazonium salt for the formation of the colored azo compound.

However, for a diagnostic agent for the rapid and simple detection of leukocytes in body fluids, for example in urine, two-component systems of this kind prove to be unsuitable since, as is known, many compounds present in urine, for example urobilinogen, stercobilinogen, bilirubin and the like, react with diazonium salts. Furthermore, this detection method is much too insensitive. Thus, for example, samples containing 5000 leukocytes/μl. show no reaction.

Surprisingly, we have now found that stable and rapidly indicating diagnostic agents, with which leukocytes can readily be detected in body fluids, are obtained when, as substrate for the detection of the esterases present in the neutrophilic leukocyte granulocytes, there are used sulphonphthalein esters.

Thus, according to the present invention, there is provided a diagnostic agent for the detection of leukocytes in body fluids, comprising an absorbent carrier which is impregnated with a chromogen and conventional additives, wherein, as substrate for the detection of the esterases present in the leukocytes, there is used a sulphonphthalein ester of the general formula:

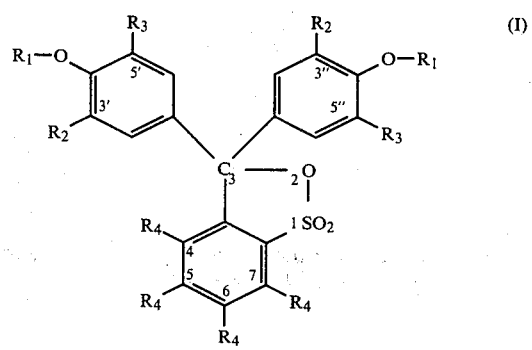

in which $R_1$ is a carboxylic acid residue optionally substituted by halogen or a lower alkoxy radical or is an amino acid or peptide residue provided with a nitrogen-protecting group which is conventional in peptide chemistry, $R_2$ is a halogen atom or a lower alkyl radical and $R_3$ and $R_4$, which can be the same or different, are hydrogen or halogen atoms.

The present invention is also concerned with the use of the sulphonphthalein esters of general formula (I) for the preparation of diagnostic agents for the detection of leukocytes in body fluids.

Most of the sulphonphthalein esters of general formula (I) are new compounds, the only ones which are known from the literature being diacetyl-3',5',3",5"-tetrabromophenolsulphonphthalein (bromophenol blue diacetate) and dibenzoyl-3',5',3",5"-tetrabromophenolsulphonphthalein (bromophenol blue dibenzoate) (see W. R. Orndorff, F. W. Sherwood, J.A.C.S., 45, 486/1923).

Thus, the present invention also provides new sulphonphthalein esters of the general formula:

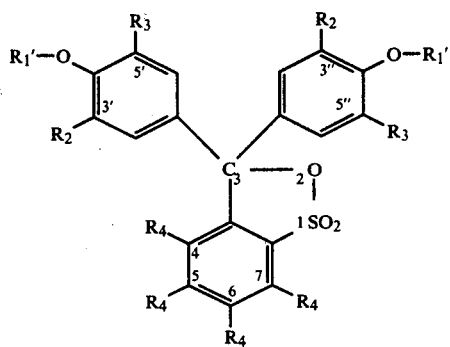

(I')

wherein $R_2$, $R_3$ and $R_4$ have the same meanings as above and $R'_1$ has the same meaning as $R_1$, with the proviso that, when $R_2$ and $R_3$ are bromine atoms and $R_4$ is a hydrogen atom, $R'_1$ does not signify an acetyl or benzoyl radical, as well as processes for the preparation thereof.

The new sulphonphthalein esters of general formula (I) can be prepared by known methods and preferably by reacting a corresponding known sulphonphthalein of the general formula:

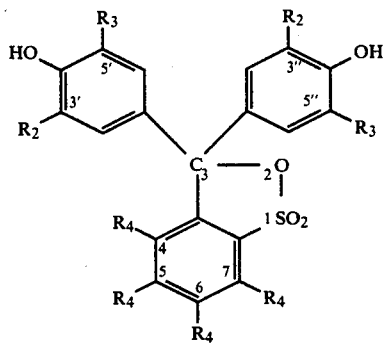

(II)

wherein $R_2$, $R_3$ and $R_4$ have the above-given meanings, with an acid of the general formula:

(III), wherein $R'_1$ has the same meaning as above, or with an appropriate reactive derivative thereof.

As reactive derivatives for the preparation of the carboxylic acid esters, there are preferably used the corresponding carboxylic acid anhydrides or carboxylic acid chlorides, optionally with the addition of tertiary amines. For the preparation of the amino acid and peptide esters, there are used the methods of synthesis which are conventional in peptide chemistry, for example the mixed anhydride and the acid chloride methods.

Halogen in the definitions of the substituents $R_1$, $R'_1$, $R_2$, $R_3$ and $R_4$ is to be understood to mean fluorine, chlorine and bromine and preferably chlorine and bromine.

The lower alkoxy radicals in the definitions of the substituent $R_1$ and $R'_1$, as well as the lower alkyl radicals of the substituent $R_2$, contain up to 5 and preferably up to 3 carbon atoms, the methoxy and methyl radicals being especially preferred.

The carboxylic acid residues of the substituents $R_1$ and $R'_1$ are residues of aliphatic carboxylic acids containing up to 7 and preferably up to 4 carbon atoms or of aromatic carboxylic acids, for example of benzoic or naphthoic acids, the acetyl, propionyl and benzoyl radicals being especially preferred.

The amino acid residue of the substituents $R_1$ and $R'_1$ are preferably the residues of natural L-α-amino acids and especially of L-alanine, L-phenyl-alanine, L-lysine, L-tyrosine and L-arginine, which can be substituted by a nitro group and hydroxyl groups possibly present can, if desired, carry a conventional oxygen protecting group, for example an acetyl radical.

The peptide residue in the definition of the substituents $R_1$ and $R'_1$ is to be understood to be a di-, tri- or tetrapeptide residue and preferably a dipeptide residue, the amino acid components preferably being those of the above-mentioned amino acids.

The sulphonphthalein esters of general formula (I) employed as chromogens can be used in concentrations of from $10^{-4}$ to $10^{-1}$ mol/liter and preferably of from $10^{-3}$ to $10^{-2}$ mol/liter of impregnation solution.

A further component of the diagnostic agent for the detection of leukocytes is an appropriate buffer system. For this purpose, there can be used, for example, a phosphate, barbiturate, borate, tris-(hydroxymethyl)aminomethane (tris), 2-amino-2-methylpropane-1,3-diol (amediol) or amino acid buffer, the pH value and the capacity thereby being so chosen that, after dipping the test strip into the body fluid, there is obtained a pH value of 6 to 10 and preferably of 7 to 9.

Furthermore, in the production of the diagnostic agent according to the present invention for the detection of leukocytes in body fluids, it is advantageous additionally to employ tensides since, in this way, shorter reaction times can be achieved. It is preferable to use cation-active wetting agents, for example quaternary pyridinium salts, in concentrations of 0.05 to 2% and preferably of 0.1 to 0.5%.

For the production of the diagnostic agent according to the present invention, preferably an absorbent carrier, for example filter paper or cellulose or synthetic resin fibre fleece, is impregnated with solutions of the reagents necessary and usually employed for the production of test strips (substrate, buffer, possibly tensides or also thickening agents, for example polyvinylpyrrolidone, carboxymethylcellulose and starch, stabilizing agents, for example amino acids, background coloring agents, for example tartrazine, and the like) in readily volatile solvents, for example water, methanol, ethanol or acetone. Impregnation is preferably carried out in two separate steps, the first of which is carried out with an aqueous solution which contains the buffer. Thereafter, a second impregnation is carried out with a solution of the esterase substrate of general formula (I). In special cases, the impregnations can also be carried out in the reversed order. The finished test papers can be used as such or struck in known manner on to handles or preferably sealed between synthetic resin films and fine-meshed materials according to German Pat. No. 2,118,455.

Diagnostic agents are obtained which, after dipping into the body fluid to be investigated, indicate rapidly and in a manner which is easy to handle, the presence of leukocytes via a color reaction. Since the activity of the esterases present in the neutrophilic leukocyte granulocytes is fully maintained even after lysis of the leukocytes, the diagnostic agent according to the present invention detects not only intact but also lysed leukocytes. Consequently, errors due to lysis do not occur.

The following Examples are given for the purpose of illustrating the present invention:

EXAMPLE 1

Filter paper (for example Schleicher and Schüll 23 SL) is successively impregnated with the following solutions and then dried at 60° C.:

Solution 1

| tris-(hydroxymethyl)-aminomethane | 0.61 g. |
|---|---|
| 0.1N hydrochloric acid | about 5 ml. |
| distilled water ad | 100 ml. |

The solution is adjusted with 0.1 N hydrochloric acid to a pH value of 9.0.

Solution 2

| diacetyl-4,5,6,7,3',5'3'',5''-octa-bromophenolsulphonphthalein (tetra-bromophenol blue diacetate) | 0.107 g. |
|---|---|
| acetone ad | 100 ml. |

A white test paper is obtained which, upon dipping into a leukocyte-containing urine, becomes blue colored.
The following detections can be made therewith:

| 5000 leukocytes/μl. | urine in about 2 minutes |
|---|---|
| 2000 leukocytes/μl. | urine in about 5 minutes |
| 1000 leukocytes/μl. | urine in about 10 minutes |
| 500 leukocytes/μl. | urine in about 15 minutes. |

The sensitivity of the test lies at about 500 leukocytes/μl.

Test papers with similar properties (sensitivities of 300 to 1000 leukocytes/μl.) are obtained when, instead of diacetyl-4,5,6,7,3',5',3'',5''-octabromophenolsulphonphthalein (tetrabromophenol blue diacetate), there are used the following substrates:

(a) diacetyl-3',3''-dichlorophenolsulphonphthalein (chlorophenol red diacetate) gives, upon dipping into leukocyte-containing urine, a red reaction product;

(b) diacetyl-5',5''-dibromo-o-cresolsulphonphthalein (bromocresol purple diacetate) gives a purple-colored reaction product;

(c) diacetyl-3',5',3'',5''-tetrabromophenolsulphonphthalein (bromophenol blue diacetate) gives a blue reaction product;

(d) diacetyl-3',3''-dibromo-5',5''-dichlorophenolsulphonphthalein (bromochlorophenol blue diacetate) gives a blue reaction product;

(e) diacetyl-4,5,6,7-tetrabromo-3',5',3'',5''-tetrachlorophenolsulphonphthalein (tetrabromotetrachlorophenol blue diacetate) gives a blue reaction product;

(f) dichloroacetyl-3',3''-dibromo-5',5''-dichlorophenolsulphonphthalein (bromochlorophenol blue dichloroacetate) gives a blue reaction product;

(g) dichloroacetyl-3',5',3'',5''-tetrabromophenolsulphonphthalein (bromophenol blue dichloroacetate) gives a blue reaction product;

(h) dichloroacetyl-4,5,6,7-3',5',3'',5''-octabromophenolsulphonphthalein (tetrabromophenol blue dichloroacetate) gives a blue reaction product;

(i) di-(2-methoxypropionyl)-4,5,6,7,3',5',3'',5''-octabromophenolsulphonphthalein (tetrabromophenol blue di-(2-methoxypropionate)) gives a blue reaction product; and (j) dibenzoyl-4,5,6,7,3',5',3'',5''-octabromophenolsulphonphthalein (tetrabromophenol blue dibenzoate) gives a blue reaction product.

EXAMPLE 2

Filter paper (for example Schleicher and Schüll 23 SL) is successively impregnated with the following solutions and then dried at 60° C.:

Solution 1

| disodium tetraborate decahydrate | 1.91 g. |
|---|---|
| 0.1 hydrochloric acid | about 20 ml. |
| distilled water ad | 100 ml. |

The solution is adjusted to a pH value of 9.0 with 0.1 N hydrochloric acid.

Solution 2

| di-(N-benzyloxycarbonyl-L-phenylalanyl)-3',5',3'',5''-tetrabromophenolsulphonphthalein (di-(N-benzyloxycarbonyl-L-phenylalanyl)-bromophenol blue) | 0.123 g. |
|---|---|
| acetone ad | 100 ml. |

A white test paper is obtained which, upon dipping into leukocyte-containing urine, becomes blue colored after about 10 minutes. The sensitivity of the test lies at about 1000 leukocytes/μl.

Test papers with similar properties (sensitivities of 300 to 3000 leukocytes/μl.) are obtained when, instead of di-(N-benzyloxycarbonyl-L-phenylalanyl)-3',5',3'',5''-tetrabromophenolsulphonphthalein, there are used the following substrates, whereby, in all cases, upon dipping into leukocyte-containing urines, blue reaction products are obtained:

(a) di-(N-benzyloxycarbonyl-L-alanyl)-3',5',3'',5''-tetrabromosulphonphthalein (di-(N-benzyloxycarbonyl-L-alanyl)-bromophenol blue);

(b) di-(Nα,Nω-dibenzyloxycarbonyl-L-lysyl)-3',5',3'',5''-tetrabromophenolsulphonphthalein (di-(N=,Nω-dibenzyloxycarbonyl-L-lysyl)-bromophenol blue);

(c) di-(N-benzyloxycarbonyl-O-acetyl-L-tyrosyl)-3',5',3'',5''-tetrabromophenolsulphonphthalein (di-(N-benzyloxycarbonyl-O-acetyl-L-tyrosyl)-bromophenol blue);

(d) di-(N-benzyloxycarbonyl-N-ethoxycarbonyl-O-acetyl-L-tyrosyl)-3',5',3'',5''-tetrabromophenolsulphonphthalein (di-N-benzyloxycarbonyl-N-ethoxycarbonyl-O-acetyl-L-trysoyl)-bromophenol blue);

(e) di-(Nα-benzyloxycarbonyl-Nω-nitro-L-arginyl)-3',5',3'',5'' tetrabromophenolsulphonphthalein (di-(N-α-benzyloxycarbonyl-Nω-nitro-L-arginyl)-bromophenol blue);

(f) di-(N-benzyloxycarbonyl-L-alanyl-L-alanyl)-3',5',3'',5''-tetrabromophenolsulphonphthalein (di-(N-benzyloxycarbonyl-L-alanyl-L-alanyl)-bromophenol blue);

(g) di-(N-benzyloxycarbonyl-L-alanyl)-4,5,6,7,3',5',3'',5''-octabromophenolsulphonphthalein (di-(N-benzyloxycarbonyl-L-alanyl)-tetrabromophenol blue.

EXAMPLE 3

Filter paper (Schleicher and Schüll 23 SL) is successively impregnated with the following solutions and then dried at 60° C.:

Solution 1

| | |
|---|---|
| tris-(hydroxymethyl)-aminomethane | 0.61 g. |
| 0.1N hydrochloric acid | about 5 ml. |
| lauryl pyridinium chloride | 0.2 g. |
| distilled water ad | 100 ml. |

The solution is adjusted to a pH value of 9.0 with 0.1 N hydrochloric acid.

Solution 2

| | |
|---|---|
| diacetyl-4,5,6,7,3',5'3'',5''-octa-bromophenolsulphonphthalein (tetrabromophenol blue diacetate) | 0.107 g. |
| acetone ad | 100 ml. |

A white test paper is obtained which, upon dipping into leukocyte-containing urines, becomes blue colored in about 1 minute. The sensitivity of the test lies at about 500 leukocytes/μl.

Test papers are also obtained in similar manner with the use of the other substrates mentioned in Examples 1 and 2, together with wetting agents, such as the above-mentioned lauryl pyridinium chloride, which, in comparison with other test papers without a wetting agent, show reaction times shortened by one half.

EXAMPLE 4

Diacetyl-4,5,6,7,3',5',3'',5''-octabromophenolsulphonphthalein (tetrabromophenol blue diacetate)

5.0 g. (5 mMol) Tetrabromophenol blue are dissolved, with warming, in 54 g. (50 ml.; 0.45 mol) freshly distilled acetic anhydride and heated under reflux for 3 hours. After concentrating the solution in a vacuum, the oily residue obtained is stirred with a little isopropanol and recrystallized from toluene. The diacetate thus obtained melts at 166°–167° C. and contains 2 mol acetic acid of crystallization which can be removed by drying over phosphorus pentoxide at 60° C. There are obtained 4.2 g. (77.4% of theory) tetrabromophenol blue diacetate in the form of colorless crystals; m.p. 174° C. (decomp.).

The following compounds are obtained in an analogous manner from the appropriately substituted phenolsulphonphthaleins:

(a) diacetyl-3',3''-dichlorophenolsulphonphthalein (chlorophenol red diacetate); colorless crystals; m.p. 132° C. (decomp.);

(b) diacetyl-5',5''-dibromo-o-cresolsulphonphthalein (bromocresol purple diacetate); colorless crystals; m.p. 117° C. (decomp.);

(c) diacetyl-3',3''-dibromo-5',5''-dichlorophenolsulphonphthalein (bromochlorophenol blue diacetate); colorless crystals; m.p. 217° C. (decomp.);

(d) diacetyl-4,5,6,7-tetrabromo-3',5',3'',5''-tetrachlorophenolsulphonphthalein (tetrabromotetrachlorophenol blue diacetate); colorless crystals; m.p. 253°–254° C. (decomp.).

EXAMPLE 5

Di-(chloroacetyl)-4,5,6,7,3',5',3'',5''-octabromophenolsulphonphthalein (tetrabromophenol blue di-(chloroacetate))

0.81 ml. (10 mMol) Anhydrous pyridine are added dropwise, with stirring, to a solution of 5.0 g. (5 mMol) tetrabromophenol blue in 100 ml. anhydrous tetrahydrofuran and, while cooling with ice, a solution of 1.18 g. (0.79 ml.; 10.5 mMol) freshly distilled chloroacetyl chloride in 3 ml. anhydrous tetrahydrofuran is added dropwise thereto at 10° C. After stirring for 2 hours at ambient temperature, the pyridine hydrochloride formed is filtered off with suction and the filtrate is evaporated in a vacuum at 50° C., 6.1 g. of an oily residue being obtained. This is boiled with 50 ml. isopropanol and insoluble material is separated off. After cooling in an ice-bath, there are obtained 3.9 g. (68.7% of theory) tetrabromophenol blue di-(chloroacetate) in the form of pale yellow crystals; m.p. 226°–227° C. (decomp.).

The following compounds are obtained in an analogous manner from the appropriately substituted phenolsulphonphthaleins and the appropriate acid chlorides:

(a) di-(chloroacetyl)-3',5',3'',5''-tetrabromophenolsulphonphthalein (bromophenol blue di-(chloroacetate); colorless crystals; m.p. 206°–207° C. (decomp.);

(b) di-(chloroacetyl)-3',3''-dibromo-5',5''-dichlorosulphonphthalein (bromochlorophenol blue di-(chloroacetate)); colorless crystals; m.p. 172° C. (decomp.);

(c) di-(2-methoxypropionyl)-4,5,6,7,3',5',3'',5''-octabromophenolsulphonphthalein (tetrabromophenol blue di-(2-methoxypropionate)); colorless crystals; m.p. 214°–216° C. (decomp.);

(d) dibenzoyl-4,5,6,7,3',5',3'',5''-octabromophenolsulphonphthalein (tetrabromophenol blue dibenzoate); colorless crystals; m.p. 196°–197° C. (decomp.).

EXAMPLE 6

Di-(N-benzyloxycarbonyl-L-alanyl)-3',5',3'',5''-tetra-bromophenolsulphonphthalein
(di-(N-benzyloxycarbonyl-L-alanyl)-bromophenol blue)

Solution 1

For the preparation of a mixed anhydride, 3.13 g. (14 mMol) N-benzyloxycarbonyl-L-alanine are dissolved in 50 ml. anhydrous tetrahydrofuran, mixed with 1.93 ml. (14 mMol) triethylamine and cooled to 31 15° to −20° C. 1.34 ml. (14 mMol) Ethyl chloroformate are then pipetted in, while stirring, and the reaction mixture left to stand for 20 to 30 minutes in a cold bath, with the exclusion of moisture.

Solution 2

4.69 g. (7 mMol) Bromophenol blue are dissolved in 45 ml. anhydrous tetrahydrofuran and cooled to −10° to −15° C.

Reaction

The triethylamine hydrochloride which precipitates out of Solution 1 during the formation of the mixed anhydride is rapidly filtered off with suction and the filtrate added to Solution 2. 2 ml. Pyridine are added thereto and the reaction mixture stirred, with the exclusion of moisture, at −15° C., carbon dioxide thereby slowly evolving.

After about 2 hours, there is added for the second time and after about 16 hours for the third time the same amount of freshly prepared, suction filtered mixed anhydride (Solution 1), whereafter stirring is continued at −15° C. for about another 5 hours.

The reaction mixture is then mixed with a few drops of water to decompose excess anhydride and the solvent subsequently distilled off in vacuum. The residue is taken up in 100 ml. ethyl acetate and successively washed with 30 ml. 1 N citric acid, 20 ml. water, 70 ml. 7% aqueous sodium bicarbonate solution and twice with 25 ml. amounts of water. After drying over anhydrous sodium sulphate, the ethyl acetate phase is evaporated in a vacuum. There are obtained 11.3 g. of a yellowish, sticky crude product which is purified by column chromatography on silica gel with a toluene-dioxan-ethyl acetate mixture (9:2:1: v/v/v). There are thus obtained 5.5 g. (68% of theory) di-(N-benzyloxycarbonyl-L-alanyl)-3',5',3'',5''-tetrabromophenolsulphonphthalein in the form of a colorless, amorphous powder; $\alpha_D^{20} = -33.6°$ (c=1% in methanol). According to the analysis, the compound also contains 0.39 mol water, 0.19 mol dioxan and 0.60 mol toluene.

The following compounds are obtained in an analogous manner by the reaction of appropriately substituted phenolsulphonphthaleins with appropriate amino acids:

(a) di-(N-benzyloxycarbonyl-L-phenylalanyl)-3',5',3'',5''-tetrabromophenolsulphonphthalein
(di-(N-benzyloxycarbonyl-L-phenylalanyl)-bromophenol blue); colorless, amorphous powder; $\alpha_D^{20} = -33.5°$ (c=1% in ethyl acetate);

(b) di-N$_\alpha$N$_\omega$-di-(benzyloxycarbonyl)-L-lysyl)-3',5',3'',5''-tetrabromophenolsulphonphthalein
(di-(N$_\alpha$,N$_\omega$-di-(benzyloxycarbonyl)-L-lysyl)-bromophenol-blue); colorless, amorphous powder; $\alpha_D^{20} = -15.0°$ (c=1% in ethyl acetate);

(c) di-(N-benzyloxycarbonyl-O-acetyl-L-tyrosyl)-3',5',3'',5''-tetrabromophenolsulphonphthalein
(di-(N-benzyloxycarbonyl-O-acetyl-L-tyrosyl)-bromophenol blue); colorless, amorphous powder which contains 0.6 mol ethyl acetate; $\alpha_D^{20} = -35.3°$ (c=1% in ethyl acetate).

As by-product of the synthesis, there is hereby also obtained:
di-(N-benzyloxycarbonyl-N-ethoxycarbonyl-O-acetyl-L-tyrosyl)-3',5',3'',5''-tetrabromophenolsulphonphthalein
(di-(N-benzyloxycarbonyl-N-ethoxycarbonyl-O-acetyl-L-tyrosyl)-bromophenol blue); colorless, amorphous powder; $\alpha_D^{20} = -19.5°$ (c=1% in ethyl acetate);

(d) di-(N-benzyloxycarbonyl-L-alanyl)-4,5,6,7,3',5',3'',5''-octabromophenolsulphonphthalein
(di-(N-benzyloxycarbonyl-L-alanyl)-tetrabromophenol blue); colorless, amorphous powder; $\alpha_D^{20} = -28.7°$ (c=1% in methanol).

EXAMPLE 7

Di-(N-benzyloxycarbonyl-L-alanyl-L-alanyl)-3',5',3'',5''-tetrabromophenolsulphonphthalein
(di-(N-benzyloxycarbonyl-L-alanyl-L-alanyl)-bromophenol blue)

Solution 1

For the preparation of the acid chloride by the one-step method, 1.18 g. (4 mMol) N-benzyloxycarbonyl-L-alanine-L-alanine is dissolved in 10 ml. anhydrous dimethylformamide and cooled to −30° C. Then, while stirring and cooling, 0.32 ml. (4.4 mMol) thionyl chloride are pipetted thereto and the reaction mixture left to stand for 30 minutes in a cold bath at −30° C., with the exclusion of moisture.

Solution 2

1.34 g. (2 mMol) Bromophenol blue are dissolved in 10 ml. anhydrous dimethylformamide and cooled to −10° to −20° C.

Reaction

Solution 2 is added to Solution 1, 1 ml. pyridine is added thereto and the reaction mixture is stirred for 2 hours at −10° to −20° C. and then for 2 hours at ambient temperature. The same amount of freshly prepared acid chloride (Solution 1), as well as pyridine, are then again added three times, in each case while maintaining the above-mentioned reaction conditions.

The reaction mixture is then evaporated to dryness in a vacuum and subsequently further worked up in the manner described in Example 6. There are obtained 2.67 g. of amorphous crude product which is purified by column chromatography on silica gel with a heptane-ethyl acetate mixture (1:2 v/v). There is obtained 1.4 g. (57% of theory) di-(N-benzyloxycarbonyl-L-alanyl-L-alanyl)-3',5',3'',5''-tetrabromophenolsulphonphthalein in the form of a colorless, amorphous powder which contains 0.6 mol ethyl acetate; $\alpha_D^{20} = -5.9°$ (c=1% in ethyl acetate).

The following compound is obtained in an analogous manner:
di-(N$_\alpha$-benzyloxycarbonyl-N$_\omega$-nitro-L-arginyl)-3',5',3'',5''-tetrabromophenolsulphonphthalein
(di-N$_\alpha$-benzyloxycarbonyl-N$_\omega$-nitro-L-arginyl)-bromophenol blue; colorless, amorphous powder which contains 0.6 mol chloroform; $\alpha_D^{20} = -12.0°$ (c=1% in glacial acetic acid).

It will be understood that the specification and examples are illustrative, but not limitative of the present invention and that other embodiments within the spirit and scope of the invention will suggest themselves to those skilled in the art.

We claim:

1. Diagnostic agent for the detection of leukocytes in body fluids, comprising an absorbent carrier which is impregnated with a chromogen and a buffer substance, wherein the chromogen is a sulfonphthalein ester of the formula

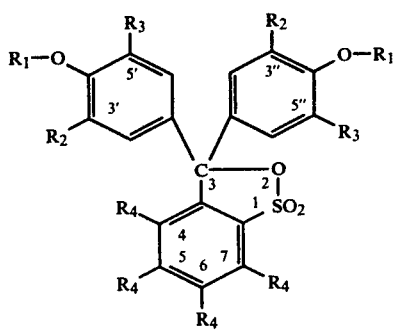

wherein
$R_1$ is an amino acid or peptide residue having a nitrogen protective group;
$R_2$ is a halogen atom or a lower alkyl radical; and
$R_3$ and $R_4$ are individually selected from hydrogen and halogen.

2. Diagnostic agent as claimed in claim 1 wherein $R_1$ in the formula is an amino acid residue.

3. Diagnostic agent as claimed in claim 1 wherein $R_1$ in the formula is a peptide residue.

4. Sulfonphthalein ester of the formula

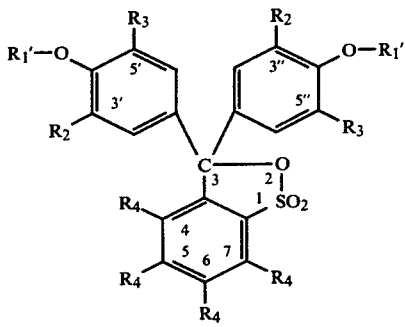

wherein
$R_1$ is an amino acid or peptide residue having a nitrogen protective group; and
$R_2$, $R_3$ and $R_4$ are individually selected from hydrogen and halogen.

5. Sulfonphthalein ester as claimed in claim 4 wherein $R'_1$ in the formula is an amino acid residue.

6. Sulfonphthalein ester as claimed in claim 4 wherein $R'_1$ in the formula is a peptide residue.

7. Sulfonphthalein ester as claimed in claim 4 wherein $R_2$ and $R_3$ are bromine, $R_4$ is hydrogen and $R'_1$ is an amino acid residue.

8. Sulfonphthalein ester as claimed in claim 4 wherein $R_2$ and $R_3$ are bromine, $R_4$ is hydrogen and $R'_1$ is a peptide residue.

9. Sulfonphthalein ester designated di-(N-benzyloxycarbonyl-L-alanyl)-3',5',3",5"-tetrabromophenolsulfonphthalein.